(12) United States Patent
Supattanasiri et al.

(10) Patent No.: US 6,371,445 B1
(45) Date of Patent: Apr. 16, 2002

(54) LOW PRESSURE VENT

(75) Inventors: Gaupongse G. Supattanasiri; Robert E. Scharfenberg, both of St. Louis, MO (US)

(73) Assignee: Essex Manufacturing Company, St. Louis, MO (US)

( * ) Notice: Subject to any disclaimer, the term of this patent is extended or adjusted under 35 U.S.C. 154(b) by 0 days.

(21) Appl. No.: 09/710,513

(22) Filed: Nov. 9, 2000

Related U.S. Application Data
(60) Provisional application No. 60/164,630, filed on Nov. 10, 1999.

(51) Int. Cl.[7] ............................................. F16K 24/00
(52) U.S. Cl. ..................... 251/368; 251/333; 251/320
(58) Field of Search ................. 251/320, 319, 251/318, 368, 333

(56) References Cited

U.S. PATENT DOCUMENTS

| | | | | |
|---|---|---|---|---|
| 4,337,788 A | * | 7/1982 | Seger | 251/333 X |
| 4,405,000 A | * | 9/1983 | Fuller | 251/320 X |
| 4,883,204 A | * | 11/1989 | Kay et al. | 251/321 X |

* cited by examiner

*Primary Examiner*—Kevin Lee
(74) *Attorney, Agent, or Firm*—Peter S. Gilster; Greensfelder, Hemker & Gale, P.C.

(57) ABSTRACT

A pressure release valve which is simple, compact, and easy to assemble for small applications, such as may be found in a flow control device on an oxygen container. A poppet of the valve has a resilient compressible cone providing spring-like characteristics to the poppet, eliminating any requirement for a separate spring, so that the pressure release valve is springless. A stem of the poppet carries a button manual actuation of the poppet. The cone resides in a slightly compressed state within a valve chamber, and the stem is loosely fitted inside the bore of a threaded insert. The poppet is normally seated in a sealing relationship with the insert. Pressing the button shifts the poppet toward an inner valve chamber, compressing the cone further, and allowing the release of gas about the stem. The resilient cone restores the sealing relationship upon button release.

10 Claims, 2 Drawing Sheets

LOW PRESSURE VENT

CROSS REFERENCE TO RELATED APPLICATION

This application claims the priority of U.S. provisional patent application Ser. No. 60/164,630, filed Nov. 10, 1999 entitled Low Pressure Vent of the present inventors which application, continued preservation of which is requested.

BACKGROUND OF THE INVENTION

1. Field of the Invention

The present invention relates to pressure release valves and more particularly to a novel, highly advantageous low pressure vent which may be utilized in systems for handling and storing pressurized fluids or gases, such as oxygen, in containers.

2. Related Art

Gas delivery systems typically consist of a pressurized gas filled container utilizing a regulator connected to a post valve of a container, such that gas will depart the container through the post valve and enter the regulator. The regulator releases a constant flow of gas into its desired destination, such as an oxygen mask, at a user selected level. When the post valve is closed which disrupts the flow of pressurized gas from the container, gas that has already left the container may become trapped between the post valve and regulator in a valve chamber of the regulator. When the regulator is subsequently disconnected from the post valve, the trapped gas which may be highly pressurized is released rapidly into the atmosphere. This rapid release of certain gases can be dangerous, such as when the container is filled with oxygen gas and combustible materials, such as plastic tubing, come in contact with the gas.

Pressure release valves prevent combustion by bleeding trapped gas out of the valve chamber. Pressure release valves are highly desirable in medical oxygen systems, including systems for patient home use, to bleed off pressurized oxygen that might otherwise have a potential for danger or pose a risk, such as by igniting combustible material. However, pressure release valves are not frequently incorporated within valve assemblies because of the difficulty of installation and the size constraints of the valve assembly.

Pressure release valves are impractical to implement in the limited space of a small valve chamber, such as may be found in a regulator. Existing pressure release valves are presently known to incorporate a poppet to seal and unseal a valve chamber and thereby selectively release pressurized gas. A spring pushes a cone of the poppet against an inner surface of the valve chamber thereby securing the poppet and sealing the valve chamber.

Incorporating a pressure release valve into a valve chamber of a regulator at the time of this invention has been impractical because suitable springs are difficult to design and install. Springs of approximately one-quarter of an inch are difficult to manufacture and are cost prohibitive to incorporate into a regulator design. Further, it is difficult to compress small springs evenly into small valve assemblies. Moreover, the addition of such small springs, which may be prone to breakage due to workmanship or incorrect installation, may compromise the reliability of the valve. These difficulties have made the design of a springless pressure relief valve desirable.

SUMMARY OF THE INVENTION

Accordingly, among the several objects, features and advantages of the invention may be noted the provision of a pressure relief valve which is springless, which has a simple design, requiring a minimum number of parts, and is easy and quick to install. It is a further feature and advantage that this pressure release valve is, because of its springless nature, inherently extremely compact.

The resilient yet compressible cone is a significant improvement over the known art. Pressure release valves typically use springs between a cone and a valve chamber for compression. These pressure release valves are difficult to install in small applications, such as on a flow selector, where there is inadequate room to utilize a spring. Also, in such small applications, there is difficulty in positioning the spring so that it does not compress awkwardly and favor one direction over another. The installation of the novel poppet is quick and reliable, and requires no spring aligning.

Briefly, the invention relates to improvements in pressurized gas flow control devices. Such a device may include a pressurized gas control body in which pressurized gas is provided from a pressurized source. The flow control device can selectively connect or disconnect a pressurized gas flow connection to the control body. More specifically, the improvement relates to such a springless pressure relief device incorporated integrally into the flow control. The relief device relieves gas pressure within the control body before connecting or disconnecting the flow connection. The relief device has a valve member movable within a valve member chamber and juxtaposed between a rigid surface of the chamber and a seat for the valve member, which is normally sealed by the valve member. The seat of the valve member communicates exteriorly of the control body. The chamber communicates with the control body for receiving gas pressure within the control body. The valve member is formed at least in part of a resilient material which is maintained in contact with the rigid surface so as to urge the valve member along said axis in a direction against said seat for providing the normal sealing relationship. The resilient material is compressible, however, so that the valve member can be selectively shiftable by compressing the resilient material along the axis toward the rigid surface for unseating of the valve member from the seat. Such shifting unseats the valve member from its seat to vent pressurized gas pressure exteriorly of the pressurized gas control body.

Other objects, features, and advantages will be apparent or are point out more particular herein below.

BRIEF DESCRIPTION OF THE DRAWINGS

Corresponding reference characters identify corresponding elements throughout the views of the drawings.

DESCRIPTION OF A PRACTICAL EMBODIMENT

Figure 1:
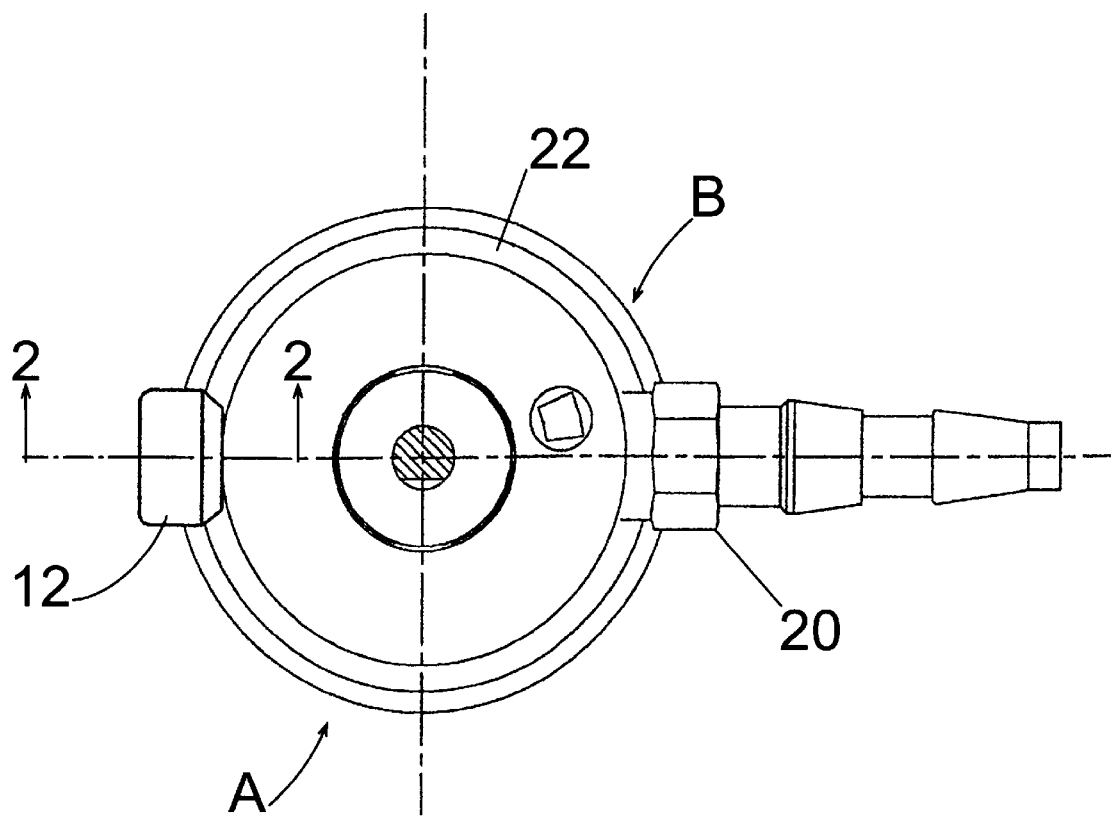
FIG. 1 is a cross-sectional view of the low pressure vent in accordance with and embodying the present invention.

Referring to FIG. 1, there is shown the low pressure vent A and which is also referred to as pressure release valve A, as located on a valve assembly such as a flow selector B, as used in a pressurized breathing oxygen system for patient use. Pressure release valve A comprises in its entirety four elements: poppet 1, gasket 18, insert 10, and button 12.

Poppet 1 is comprises of a cone 2 and stem 4. Cone 2 has a resilient yet compressible head that closes pressure release valve A when it seals against insert 10. Cone 2 is preferably a fluorocarbon or synthetic rubber, and preferably one commercially available under the trade designation VITON. The durometer hardness of cone 2 may be in the range of 40–100, preferably in the rage of 70–90, and satisfactorily of a value of 70. It should appreciated that the use of poppet 1 in applications beyond oxygen systems may require a higher cone durometer hardness valve. Cone 2 is juxtaposed to inner wall 3 of valve chamber 8, so that it is compressed slightly against inner wall 3, to cause poppet 1 to be seated against insert 10. Stem 4 is fitted at least slightly loose within a bore 11 formed in insert 10 to permit venting of pressurized gas if poppet 1 is selectively unseated.

Stem 4 is preferably a durable material such as brass. However, poppet 1 may be constructed of the same resilient material for both cone 2 and stem 4. Stem 4 extends outwardly from valve chamber 8 along an axis 26 and through bore 11 with an outer portion 28 of stem 4 preferably threaded to permit an operating button 12 of desired shape to be attached, being of shape selected appropriately for the use intended, as to permit thumb actuation. Threaded engagement with stem 4 provides for easy removal and interchange of various buttons 12 or other operating devices (not shown).

Gasket 18 provides a tight seal between valve body 20 and insert 10 when the latter is seated, as by being fitted into threads of valve body 20. Gasket 19, which functions similarly to gasket 18, may instead be in the form of an O-ring.

Insert 10, while made of a brass alloy according to the present embodiment, may also be made of any other suitable material, but should not allow gas to seep around gasket 18,19, or otherwise permit leakage of pressurized gas from the interior of pressure release valve A. Insert 10, while herein described as threaded, may be of another suitable design to provide an effective sealing relationship between insert 10 and valve body 20.

When pressure is exerted along axis 26 against button 12 or the end of poppet 1, cone 2 is further compressed to create a slight passageway between poppet 1 and its seat 30, so that gas vents between loosely fitted poppet stem 4 and bore 11. The tolerance between stem 4 and bore 11 may be selected to control the rate of venting. Venting grooves and other expedients may also or alternatively be employed. The pressurized gas is thus dissipated harmlessly, but its release is gradual because of the selected relative dimensions of poppet 1 and stem 4 within bore 11. In practical use, the dimensions may be selected so that venting upon depressing button 12 will require a small number of seconds, so as to achieve a gentle and gradual release. When button 12 is released, poppet 1 returns to its original slightly compressed state, thereby seating itself because of its own resilience, so that the passageway closes.

Figure 2:
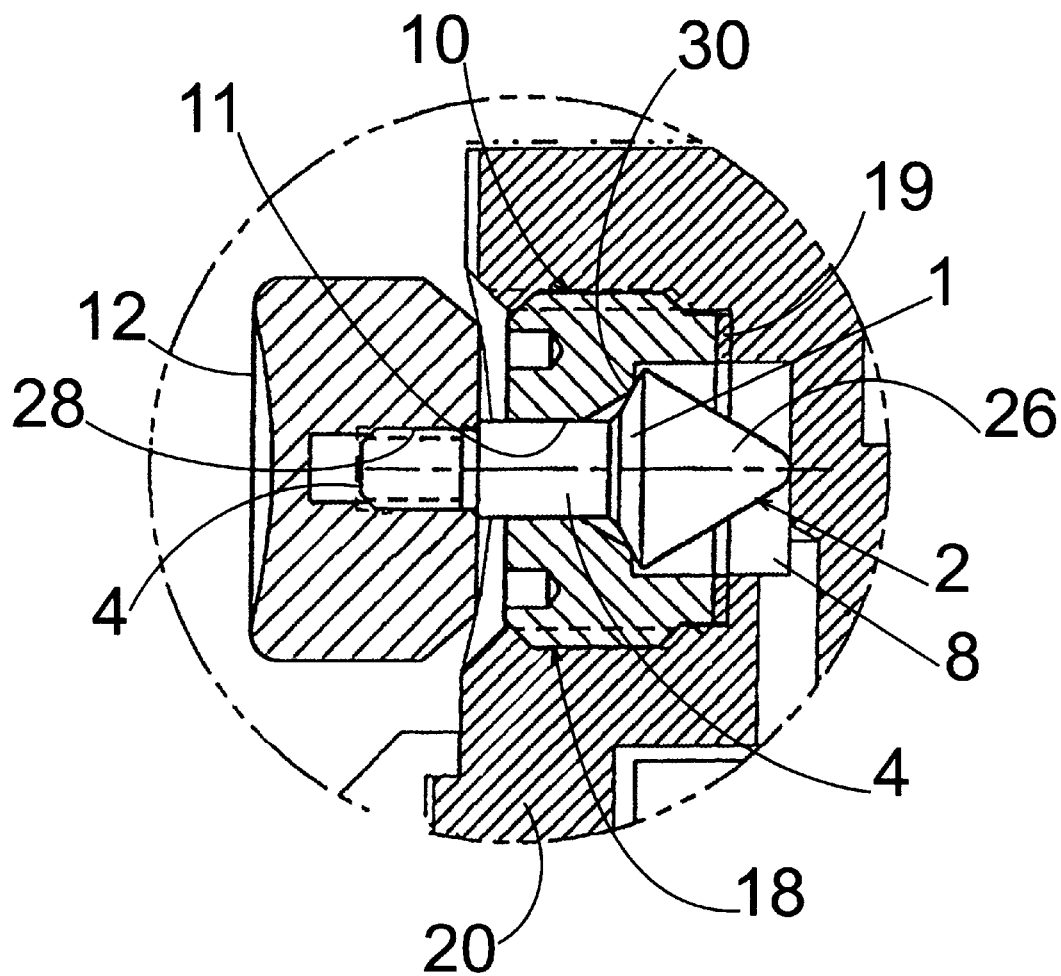
FIG. 2 is a cross-sectional view of the flow selector taken along line 2—2 from FIG. 1 in which the new low pressure vent is incorporated.

FIG. 2 shows flow selector B in which pressure release valve A has been incorporated. Button 12 extends from a side opposite valve body 20, which are located on opposing ends of flow selector casing 22.

The small number of elements of the low pressure vent A allows simple and rapid assembly, and so greatly facilitating its installation within valve body 20.

In view of the foregoing description of the present invention and various embodiments and methods it will be seen that the several objects of the invention are achieved and other advantages are attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. In a pressurized gas flow control device including a pressurized gas control body to which is provided pressurized gas from a source of pressurized gas under pressure, and means for selectively connecting or disconnecting a pressurized gas flow connection to the pressurized gas control body, the improvement comprising a pressure relief device for relieving pressurized gas pressure within the pressurized gas control body before disconnecting the pressurized gas flow connection, the pressure relief device comprising a valve member movable for operation along an axis of movement within a valve member chamber in which the valve member is juxtaposed between a rigid surface of the chamber and a seat for the valve member, the seat communicating exteriorly of the pressurized gas control body, the chamber communicating with the pressurized gas control body for receiving pressurized gas pressure within the pressurized gas control body, the valve member being formed at least in part of a resilient material contacting the rigid surface and urging the valve member along said axis in a direction against said seat for providing a sealing relationship, the resilient material being compressible, the valve member being selectively shiftable by compressing of the resilient material along said axis toward the rigid surface for unseating of the valve member from the seat to vent pressurized gas pressure to exteriorly of the pressurized gas control body.

2. The improvement according to claim 1 further characterized in that the pressurized gas is oxygen.

3. The improvement according to claim 2 further characterized in the valve member is configured such that pressure of oxygen with the valve member chamber urges the valve member into sealing relationship against the seat.

4. The improvement according to claim 3 wherein the valve member is configured generally in the form of a base seated against said seat and reduces in cross-sectional area to a tip in contact with the rigid surface, an operating extension extending from the base outwardly of the pressurized gas control body as an actuating member for manual actuation, the tip being resiliently compressed as the valve member is selectively shiftable by manual actuation of the actuating member by pressing inwardly of the pressurized gas control body for causing unseating of the valve member from the seat to cause venting of the pressurized gas control body, the resiliently compressed tip urging the valve member again into sealing relation with the seat upon release of the actuating member.

5. The improvement according to claim 4 wherein the valve member is configured generally in the form of a cone, wherein the cone defines said tip.

6. The improvement according to claim 5 wherein the cone is of VITON.

7. An apparatus for selectively releasing trapped pressurized gas from a chamber, the apparatus comprising:
- a poppet having a cone and a stem attached to a base of the cone, wherein the cone is of resilient, compressible material;
- an insert securely positioned within the chamber for retaining the poppet, the cone residing in a slightly compressed state within the chamber, the stem extending from the chamber through an aperture of the insert, the poppet being normally seated in a sealing relationship against the insert, with the stem in loosely fitting relationship within the insert, for preventing the gas normally from being released from the chamber; and
- the stem being capable of being selectively operated for urging the poppet in a direction toward the chamber for compressing the cone thereby to allow release of pressurized gas about the stem.

8. The apparatus of claim 7, wherein said cone is a fluorocarbon.

9. The apparatus of claim 7, wherein said cone is a synthetic rubber.

10. The apparatus of claim 7, wherein said cone is VITON.

* * * * *